United States Patent
Brogaard et al.

(10) Patent No.: US 9,901,869 B2
(45) Date of Patent: Feb. 27, 2018

(54) METHOD OF CONTROLLING A WET SCRUBBER USEFUL FOR REMOVING SULPHUR DIOXIDE FROM A PROCESS GAS

(71) Applicant: ALSTOM Technology Ltd, Baden (CH)

(72) Inventors: Fredrik Jens Brogaard, Växjö (SE); Kerstin Margareta Forsgren, Växjö (SE); Mikael Larsson, Mölndal (SE); Rikard BjoernSture Håkansson, Växjö (SE)

(73) Assignee: General Electric Technology GmbH, Baden (CH)

( * ) Notice: Subject to any disclaimer, the term of this patent is extended or adjusted under 35 U.S.C. 154(b) by 72 days.

(21) Appl. No.: 15/231,899

(22) Filed: Aug. 9, 2016

(65) Prior Publication Data

US 2016/0346730 A1    Dec. 1, 2016

Related U.S. Application Data (62) Division of application No. 14/346,896, filed as application No. PCT/IB2012/055435 on Oct. 8, 2012, now Pat. No. 9,440,183.

(30) Foreign Application Priority Data

Oct. 7, 2011    (EP) ..................... 11184434

(51) Int. Cl.
   *B01D 53/14*    (2006.01)
   *A61L 9/00*    (2006.01)
   (Continued)

(52) U.S. Cl.
   CPC ....... *B01D 53/346* (2013.01); *B01D 53/1481* (2013.01); *B01D 53/504* (2013.01);
   (Continued)

(58) Field of Classification Search
   CPC .... B01D 2257/2045; B01D 2257/2047; B01D 2257/302; B01D 2257/602; B01D 53/1481; B01D 53/346; B01D 53/504
   See application file for complete search history.

(56) References Cited

U.S. PATENT DOCUMENTS

| | | |
|---|---|---|
| 5,560,893 A | 10/1996 | Okino et al. |
| 5,686,053 A | 11/1997 | Kikkawa et al. |
| 5,693,301 A | 12/1997 | Ahman |

FOREIGN PATENT DOCUMENTS

| | | |
|---|---|---|
| CN | 101048709 B | 7/2010 |
| EP | 0 108 280 A1 | 5/1984 |

(Continued)

OTHER PUBLICATIONS

Dou et al.—Prediction of SO2 Removal Efficiency for Wet Flue Gas Dsulfurization—Oct. 1, 2009 (Oct. 1, 2009) Energy Conversion and Management.

(Continued)

*Primary Examiner* — Cabrena Holecek
(74) *Attorney, Agent, or Firm* — GE Global Patent Operation; Rita D. Vacca (57) ABSTRACT

A wet scrubber for cleaning a process gas containing sulphur dioxide comprises an absorption vessel for contacting the process gas with an absorption liquid to absorb sulphur dioxide from the process gas, a sensor for measuring a concentration in the absorption liquid, and a control unit. The control unit is adapted to receive a measurement signal from the sensor and to control, based on the measured concentration, at least one wet scrubber operating parameter influencing the concentration in the absorption liquid.

9 Claims, 8 Drawing Sheets

(51) Int. Cl.
  *B01D 53/34* (2006.01)
  *B01D 53/50* (2006.01)
  *B01D 53/78* (2006.01)
  *B01D 53/80* (2006.01)
  *G01N 33/00* (2006.01)

(52) U.S. Cl.
  CPC .............. *B01D 53/78* (2013.01); *B01D 53/80* (2013.01); *G01N 33/0042* (2013.01); *B01D 2251/404* (2013.01); *B01D 2251/606* (2013.01); *B01D 2252/602* (2013.01); *B01D 2257/2045* (2013.01); *B01D 2257/2047* (2013.01); *B01D 2257/302* (2013.01); *B01D 2257/602* (2013.01)

(56) References Cited

FOREIGN PATENT DOCUMENTS

| | | | | |
|---|---|---|---|---|
| EP | 0 162 536 | A1 | 11/1985 | |
| EP | 0 824 953 | A1 | 2/1998 | |
| EP | 1 040 864 | A2 | 10/2000 | |
| EP | 1 219 957 | A1 | 7/2002 | |
| EP | 1 010 005 | B1 | 7/2008 | |
| GB | 2 159 508 | A | 12/1985 | |
| GB | 2159508 | A * | 12/1985 | ........... B01D 53/501 |
| TW | 276189 | B | 5/1996 | |
| TW | 288986 | B | 10/1996 | |
| TW | 505534 | B | 10/2002 | |
| WO | 96/14137 | | 5/1996 | |
| WO | 99/13325 | | 3/1999 | |
| WO | 02/44460 | A1 | 6/2002 | |
| WO | 02/052254 | A1 | 7/2002 | |
| WO | 03/046554 | A1 | 6/2003 | |
| WO | 2005/007274 | A1 | 1/2005 | |

OTHER PUBLICATIONS

Labrador et al.—"Determination of Bisulfites in Wines with an Electronic Tongue Based on Pulse Voltammetry"—Electroanalysis 2009, 21, No. 305, 612-617.
Winquist et al.—"An Electronic tongue based on voltammetry"—Analytica Chimica Acta 357 (1997) 21-31.
Winquist et al.—"Electronic Tongues"—MRS Bulletin?Oct. 2004.
European Search Report dated Jul. 25, 2012 (Jul. 25, 2012) corresponding to EP Application No. 11184434.6.
Temple, C.A., et al., "Optimization of Expression of Human Sulfite Oxidase and Its Molybdenum Domain," published in Arch Biochem Biophys., vol. 383, No. 2, pp. 281-287 (Nov. 15, 2000).
Wold, S., et al., "PLS-regression: a basic tool of chemometrics," Chemometrics and Intelligent Laboratory Systems, vol. 58, No. 2, pp. 109-130 (2001).
Wold, S., et al., "Principal Component Analysis: A tutorial," Chemometrics and Intelligent Laboratory Systems, vol. 2, No. 1-3, pp. 37-52 (Aug. 1987).

\* cited by examiner

METHOD OF CONTROLLING A WET SCRUBBER USEFUL FOR REMOVING SULPHUR DIOXIDE FROM A PROCESS GAS

CROSS-REFERENCE TO RELATED APPLICATIONS

This is a divisional application of currently pending U.S. application Ser. No. 14/346,896 filed Mar. 24, 2014, which claims priority to International Application No. PCT/IB2012/055435 having an International Filing Date of Oct. 8, 2012, and EP Application No. 11184434.6 having a Filing Date of Oct. 7, 2011, each incorporated herein in its entirety by reference.

FIELD OF THE INVENTION

The present invention relates to a method of controlling a wet scrubber useful for cleaning a process gas containing sulphur dioxide.

The present invention also relates to a wet scrubber useful for cleaning a process gas containing sulphur dioxide.

BACKGROUND OF THE INVENTION

In the combustion of a fuel such as coal, oil, peat, waste, etc., in a combustion plant such as a power plant, a hot process gas is generated that contains among other components, sulphur oxides, such as sulphur dioxide, $SO_2$. Sulphur dioxide is an environmental pollutant. Hence, it is necessary to remove at least a portion of the sulphur dioxide from the process gas before the process gas can be released into the atmosphere.

EP 0 162 536 discloses a wet scrubber in which an absorption liquid containing limestone is brought into contact with a process gas to absorb at least a portion of the content of sulphur dioxide, $SO_2$, of the process gas. The absorbed sulphur dioxide forms, in the wet scrubber, gypsum, which may be disposed of or used as a useful product in the production of gypsum wall board.

SUMMARY OF THE INVENTION

An object of the present invention is to provide a wet scrubber and a method of controlling a wet scrubber to clean a process gas containing sulphur dioxide in a manner more efficient than that of the prior art.

This object is achieved by means of a method of controlling a wet scrubber useful for cleaning a process gas containing sulphur dioxide, the method comprising:

contacting the process gas with an absorption liquid in an absorption vessel to absorb sulphur dioxide from the process gas, measuring the concentration of sulphite in the absorption liquid, and controlling, based on the measured concentration of sulphite, at least one scrubber operating parameter influencing the concentration of sulphite in the absorption liquid.

An advantage of this method is that the scrubber may be controlled to operate as efficiently as possible with regard to sulphur dioxide removal efficiency and/or energy efficiency, without causing associated problems related to high sulphite levels in the absorption liquid. Furthermore, variations in the wet scrubber operation caused by, for example, variations in the concentration of sulphur dioxide in the process gas, variations in the oxidation ratio in the absorption liquid, and/or variations in the flow of process gas, may be accounted for such that optimum scrubber operation is maintained during such varying conditions.

According to one embodiment the method further comprises comparing a measured concentration of sulphite to a set point therefore, and effecting, when the measured concentration of sulphite in the absorption liquid exceeds the set point, at least one of: increasing a supply of a gas containing oxygen to the absorption liquid, reducing a pH of the absorption liquid, and/or supplying an absorption enhancing additive to the absorption liquid. An advantage of this embodiment is that the scrubber can be operated with the lowest possible energy and/or absorbent material consumption required to keep the sulphite concentration at a suitable level. According to similar principles, an oxidation arrangement supplying a gas containing oxygen to the absorption liquid may be controlled to reduce the supply of the gas, and/or the pH of the absorption liquid may be increased, and/or the supply of an absorption enhancing additive to the absorption liquid may be reduced, when the measured concentration of sulphite in the absorption liquid falls below the set point.

According to one method embodiment, reduction of the pH of the absorption liquid is accompanied by at least one of: increasing the liquid to gas ratio in the absorption vessel, or increasing a supply of an absorption enhancing additive to the absorption liquid. An advantage of this embodiment is that the wet scrubber removal efficiency of sulphur dioxide from the process gas may be maintained at a desired level, even during periods of reduced pH to control the concentration of sulphite.

According to one embodiment, the method further comprises collecting absorption liquid after such absorption liquid has absorbed sulphur dioxide, and measuring the concentration of sulphite in the collected absorption liquid prior to mixing the absorption liquid with an absorbent material. An advantage of this embodiment is that sulphite is measured in a low pH absorption liquid, which is beneficial for accurately measuring the concentration of sulphite. Hence, improved sulphite measurement accuracy results through the use of the subject embodiment.

According to one embodiment the method further comprises collecting absorption liquid after such absorption liquid has absorbed sulphur dioxide, and measuring the concentration of sulphite in the collected absorption liquid prior to mixing the absorption liquid with an absorbent material and prior to bubbling an oxygen containing gas through such absorption liquid. An advantage of this embodiment is that sulphite may be measured with high accuracy. Furthermore, measuring sulphite in the absorption liquid prior to exposing the same to oxidation provides important information about the absorption process occurring inside the absorption vessel. For example, if the concentration of sulphite is very high in the absorption liquid collected, such may indicate that a lower portion of the absorption vessel is not contributing very much to the absorption of the sulphur dioxide. The absorption liquid is in such example, at least in the lower portion of the absorption vessel, close to the point of saturated with sulphite, with such saturation hindering further absorption of sulphur dioxide.

According to one method embodiment the concentration of sulphite is measured within 1 minute of collecting the absorption liquid from the absorption vessel. An advantage of this embodiment is that the sulphite concentration is measured just as it is inside the absorption vessel, hence avoiding interference from the natural oxidation that occurs in an absorption liquid sample as such, but which is not relevant when assessing the absorption process occurring inside the absorption vessel.

According to one embodiment, the method further comprises:

collecting absorption liquid after such absorption liquid has absorbed sulphur dioxide, and measuring a first concentration of sulphite in such absorption liquid prior to bubbling an oxygen containing gas through such absorption liquid, collecting absorption liquid after such absorption liquid has been exposed to a bubbling oxygen containing gas, and measuring a second concentration of sulphite in such absorption liquid, and comparing the first concentration of sulphite to the second concentration of sulphite to determine whether the concentration of sulphite is increasing or decreasing. An advantage of this embodiment is that rapid changes in the sulphite concentration can be detected, such that measures to reduce, or increase, as the case may be, the sulphite concentration can be initiated before a set point for the concentration of sulphite has been reached.

According to a further aspect of the invention a wet scrubber for cleaning a process gas containing sulphur dioxide is provided. The wet scrubber comprises an absorption vessel in which the process gas contacts an absorption liquid to absorb sulphur dioxide from the process gas, a sulphite sensor to measure the concentration of sulphite in the absorption liquid, and a control unit to receive a measurement signal from the sulphite sensor and to control, based on the measured concentration of sulphite, at least one wet scrubber operating parameter influencing the concentration of sulphite in the absorption liquid.

An advantage of this wet scrubber is that the removal of sulphur dioxide can be made very efficient.

According to one embodiment the wet scrubber further comprises at least one of: an oxidation arrangement oxidizing at least a portion of the content of sulphite in the absorption liquid, controlled by the control unit based on the measured concentration of sulphite; an absorption liquid supply device supplying absorption liquid to the absorption vessel, controlled by the control unit based on the measured concentration of sulphite; an absorbent supply system supplying an absorbent material to the absorption liquid, controlled by the control unit based on the measured concentration of sulphite; and an additive supply system supplying an absorption enhancing additive to the absorption liquid, controlled by the control unit based on the measured concentration of sulphite. An advantage of this embodiment is that a very efficient control of the wet scrubber can be achieved with regard to investment, operating and maintenance costs.

According to one embodiment a scoop is used for collecting absorption liquid inside of the absorption vessel after such absorption liquid has absorbed sulphur dioxide and prior to such absorption liquid mixing with absorbent material. A sulphite sensor is used to measure the concentration of sulphite in the absorption liquid collected in the scoop. An advantage of this embodiment is that highly accurate measurements of sulphite concentration are facilitated.

According to one embodiment the wet scrubber comprises a first sulphite sensor for measuring the concentration of sulphite in the absorption liquid collected in the scoop, and a second sulphite sensor for measuring the concentration of sulphite in absorption liquid collected from an absorption liquid oxidation vessel. An advantage of this embodiment is that comparing the sulphite concentrations measured by the first and second sensors provides further information about the absorption process occurring in the wet scrubber.

Further objects and features of the present invention will be apparent from the following detailed description and claims.

BRIEF DESCRIPTION OF THE DRAWINGS

The invention is described in more detail below with reference to the appended drawings in which.

DESCRIPTION OF PREFERRED EMBODIMENTS

Figure 1:
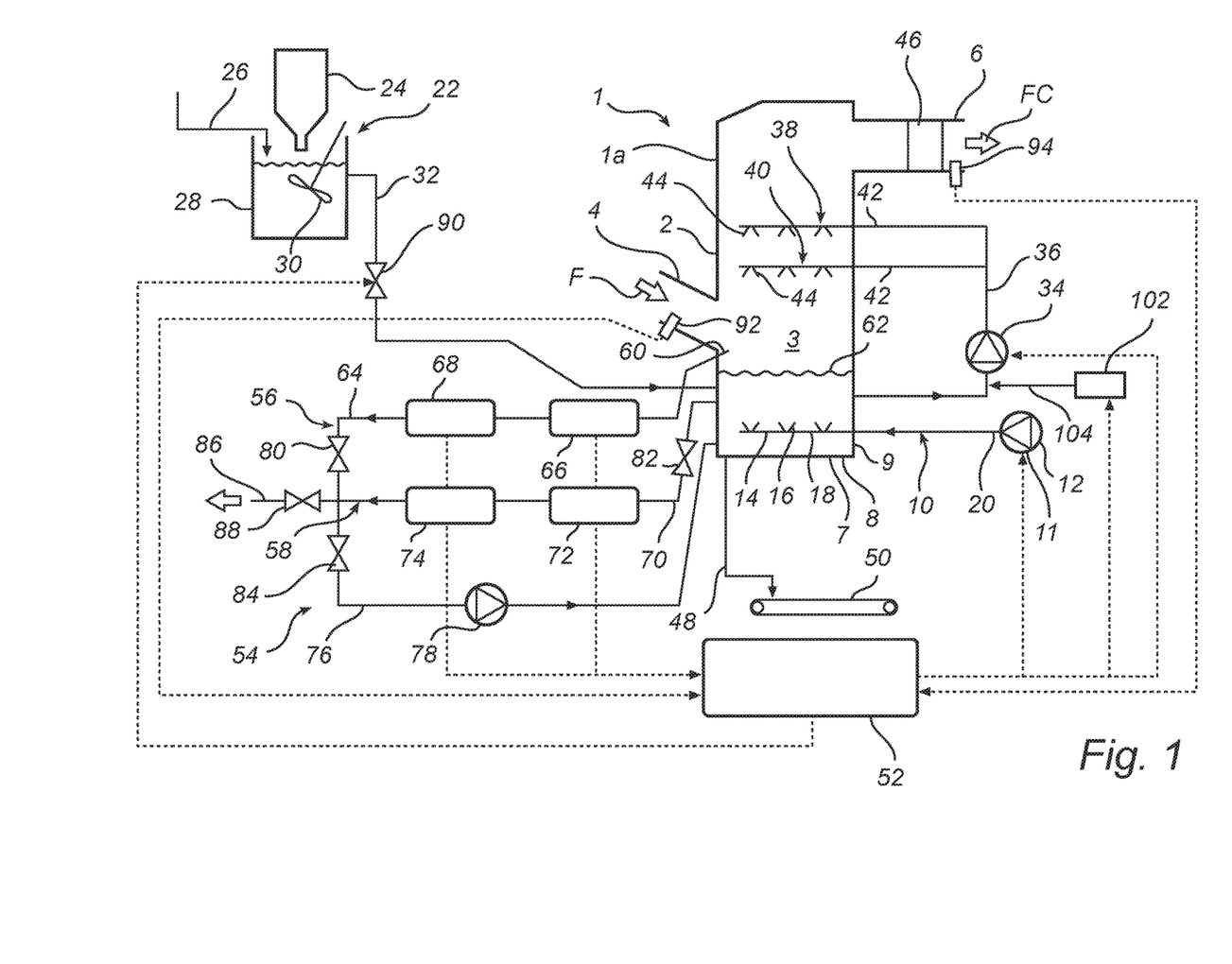
FIG. 1 is a schematic side cross sectional view of a wet scrubber in accordance with a first embodiment.

FIG. 1 illustrates a wet scrubber 1. The wet scrubber 1 is operative for removing at least a portion of the sulphur dioxide content of a process gas, in the form of a flue gas, F, generated in a boiler (not shown) for combusting a fuel, such as coal, oil, peat, natural gas, or waste material.

The wet scrubber 1 comprises an absorption vessel 1a in the form of a vertical open tower 2 with an interior 3, an inlet 4 for flue gas, F, to enter interior 3 for cleaning, and an outlet 6 for outward flow of flue gas, FC, from interior 3, with the flue gas FC having at least a portion of the sulphur dioxide content thereof removed.

An absorption liquid oxidation vessel 7 in the form of an absorption liquid tank 8 is arranged at the bottom 9 of the vertical open tower 2. The absorption liquid tank 8 fulfills dual purposes as both a recirculation tank for absorption liquid, and a vessel in which oxidation may occur. For the latter reason, the absorption liquid tank 8 is provided with an oxidation arrangement 10. The oxidation arrangement 10 comprises an oxygen gas supply device 11 in the form a blower 12, an oxygen distributor 14 comprising a number of nozzles 16 arranged on a fluidly connected distributing pipe 18, and a supply pipe 20 fluidly connected to the blower 12 and to the distributing pipe 18 for supplying compressed oxygen containing gas, such as air, to the distributing pipe 18 and further to the nozzles 16. The nozzles 16 are arranged for distributing the air in a limestone absorption liquid contained in the absorption liquid tank 8 and to cause oxidation of sulphite contained in the limestone absorption liquid, as will be described in more detail hereinafter. It will be appreciated that the oxygen supply device 11 could, as alternative to a blower, be a compressor or some other device suitable for forcing a gas containing oxygen into the absorption liquid of the absorption liquid tank 8. Furthermore, the oxygen containing gas blown by the blower 12 may, for example, be air, a rather pure oxygen gas, such as a gas comprising 90-99% by volume of oxygen, or a mixture of oxygen gas and air.

Absorbent material in the form of, for example, fresh limestone, $CaCO_3$, is supplied to the absorption liquid tank 8 from an absorbent supply system 22. The absorbent supply system 22 comprises a limestone silo 24, a water supply pipe 26, and a mixing tank 28 comprising an agitator 30. Water supplied via fluidly connected supply pipe 26 is, in the mixing tank 28, mixed with limestone powder supplied from limestone silo 24 to form limestone slurry. The limestone slurry is supplied from the mixing tank 28 to the absorption liquid tank 8 via a fluidly connected limestone supply pipe 32. It will be appreciated that absorption liquid tank 8 may, as an alternative, be positioned outside of tower 2, and that the supply of limestone could, as an alternative, enter wet scrubber 1 at other locations, as a dry powder, a slurry or both. The limestone, $CaCO_3$, may be at least partly dissolved in the water:

$$CaCO_3(s)+H_2O \Longleftrightarrow Ca^{2+}(aq)+CO_3^{-2}(aq) \quad \text{[eq. 1]}$$

The wet scrubber 1 further comprises an absorption liquid supply device in the form of one or more scrubber circulation pumps, of which one pump 34 is depicted in FIG. 1, to circulate in absorption liquid circulation pipe 36, the limestone absorption liquid, from the absorption liquid tank 8 to two spray level systems 38, 40 positioned within interior 3 of open tower 2.

Each spray level system 38, 40 comprises a piping system 42 and a number of fluidly connected atomizing nozzles 44 that finely distribute limestone absorption liquid, circulated by the pump 34, to achieve effective contact between the limestone absorption liquid and the flue gas F passing through the wet scrubber 1 and flowing substantially vertically upwards inside interior 3 of open tower 2. All or some of the atomizing nozzles 44 may, for example, be of the type 4CF-303120, available from Spraying Systems Co, Wheaton, Ill., USA. In the open tower 2 of the wet scrubber 1 the following reaction will occur upon absorption of sulphur dioxide, $SO_2$, comprised in the flue gas F by the limestone absorption liquid finely distributed by the nozzles 44:

$$SO_2(g)+Ca^{2+}(aq)+CO_3^{2-}(aq) \Longleftrightarrow Ca^{2+}(aq)+ \\ SO_3^{2-}(aq)+CO_2(g) \quad \text{[eq. 2]}$$

A mist eliminator 46 is located downstream of the spray level systems 38, 40. The mist eliminator 46 removes at least a portion of the absorption liquid droplets entrained by the cleaned flue gas, FC.

In the wet scrubber 1, sulphur dioxide, $SO_2$, in the flue gas F reacts with the limestone, $CaCO_3$, dissociated into ions as described above, to form calcium sulphite, $CaSO_3$, normally also dissociated into ions and subsequently oxidized to form solid gypsum, $CaSO_4$. The oxidation of calcium sulphite is performed by bubbling an oxygen containing gas, such as air, through the limestone absorption liquid using oxidation arrangement 10. The following reaction may occur in the absorption liquid tank 8:

$$Ca^{2+}(aq)+SO_3^{2-}(aq)+\tfrac{1}{2}O_2(g) \Longleftrightarrow CaSO_4(s)+2H_2O \quad \text{[eq. 3]}$$

Hence, gypsum, $CaSO_4$, sometimes described as including two water molecules, i.e., $CaSO_4 \times 2H_2O$, is formed as the end product. Hereinbefore, it has been described that the absorption of $SO_2$ generates calcium sulphite $CaSO_3$. It will be appreciated that, depending on the conditions, at least a portion of the absorbed $SO_2$ would generate calcium bisulphite, $Ca(HSO_3)_2$ (aq), and oxidized according to principles similar to that of [eq. 3] above.

Hence, the limestone absorption liquid comprises, in addition to the limestone, also small amounts of calcium sulphite and, as major constituent, gypsum. The gypsum formed through this process is removed from the wet scrubber 1 via a disposal pipe 48 and is forwarded to a gypsum dewatering unit, schematically illustrated in FIG. 1 as belt filter 50. The dewatered gypsum may be commercially used, for example in wallboard production.

In addition to sulphur dioxide, $SO_2$, the wet scrubber 1 will remove, at least partly, other contaminants from the flue gas. Examples of such other contaminants include sulphur trioxide, $SO_3$, hydrochloric acid, HCl, hydrofluoric acid, HF, and other acid contaminants. Still further, the wet scrubber 1 may also remove, at least partly, also other types of contaminants from the flue gas, such as for example dust particles and mercury.

A control unit 52 controls the operating parameters of wet scrubber 1. The wet scrubber 1 is provided with an absorption liquid sampling system 54 which supplies measured data to the control unit 52. The sampling system 54 comprises a direct sampling train 56 and an absorption liquid tank sampling train 58.

The direct sampling train 56 comprises a scoop 60, described in more detail below, for catching droplets of absorption liquid above a surface 62 of the absorption liquid in the tank 8. According to one embodiment the scoop 60 is positioned at least 0.5 m below the lowest nozzles 44 of the open tower 2. According to another embodiment, several scoops, such as two to six scoops, are positioned in various locations vertically along the interior 3 of open tower 2 to measure sulphite concentration at various vertical levels. According to a further embodiment the scoop 60 is positioned 1 to 300 cm above the surface 62 of the absorption liquid. The droplets of absorption liquid caught by the scoop 60 are droplets that have been atomized by nozzles 44, and have passed through the open tower 2 with absorption of sulphur dioxide, $SO_2$, but not yet been exposed to the oxidation of the oxidation arrangement 10. The droplets of absorption liquid caught by the scoop 60 have not yet contacted the absorbent material supplied via absorbent supply system 22. The absorption liquid caught by the scoop 60 flows via a fluidly connected pipe 64 to a first pH sensor 66, and a first sulphite sensor 68.

The absorption liquid tank sampling train 58 comprises a pipe 70 fluidly connected to the absorption liquid tank 8. The absorption liquid collected from tank 8 by pipe 70 flows via pipe 70, to a second pH sensor 72, and a second sulphite sensor 74. The oxidation arrangement 10 causes an agitation of the absorption liquid contained in the tank 8, and, hence, the tank 8 may be regarded as a continuously stirred tank reactor in which the oxidation reaction occurs. Optionally, a further agitator may be arranged within the tank 8.

The pipes 64 and 70 are fluidly connected to a circulation pipe 76. A circulation pump 78 is arranged in circulation pipe 76 for pumping absorption liquid, having passed through direct sampling train 56 and absorption liquid tank sampling train 58, back to absorption liquid tank 8. Shut-off valves 80, 82, 84 arranged in the pipes 64, 70 and 76, respectively, make it possible to collect an absorption liquid sample, via sampling pipe 86 and associated shut off valve 88, for manual analysis of the sulphite concentration and/or the pH of absorption liquid collected via direct sampling train 56 or absorption liquid tank sampling train 58. According to a further embodiment, the absorption liquid collected in sampling train 56 and/or sampling train 58 is drained, by gravity, back to liquid absorption tank 8, without any pump 78.

According to an alternative embodiment, the second sulphite sensor 74 could extend directly into tank 8, to measure the sulphite concentration of the absorption liquid directly inside tank 8. Such an arrangement would be less expensive, since a sampling train may not be needed, but access and serviceability may also be hampered by arranging sensor 74 in tank 8.

Control unit 52 receives measurement signals from sensors 66, 68, 72 and 74, and controls, based on such measurement signals, in a manner described in more detail below, at least one of: a control valve 90 within limestone supply pipe 32 controlling the amount of limestone slurry supplied from the mixing tank 28 to the absorption liquid tank 8, the scrubber circulation pump 34, and the blower 12 of the oxidation arrangement 10. Furthermore, the control unit 52 may also receive measurement signals from a first $SO_2$ analyzer 92 measuring the concentration of $SO_2$ in the flue gas F entering the open tower 2 of the wet scrubber 1, and a second $SO_2$ analyzer 94 measuring the concentration of $SO_2$ in the cleaned flue gas FC leaving the open tower 2 of the wet scrubber 1.

Figure 2A:
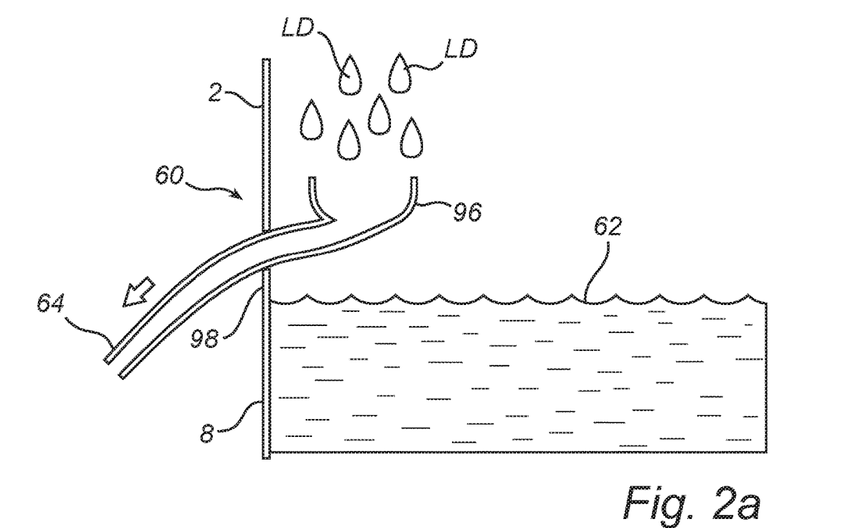
FIG. 2a is an enlarged schematic side cross sectional view of a scoop for collecting absorption liquid for measurement of sulphite concentration.

FIG. 2a illustrates the scoop 60 in more detail. The scoop 60 comprises a funnel portion 96 positioned inside interior 3 of the open tower 2, above the surface 62 of absorption liquid contained in the absorption liquid tank 8. The funnel portion 96 extends through a wall 98 of the open tower 2 and is fluidly connected to the pipe 64 of the direct sampling train 56 depicted in FIG. 1. Liquid droplets LD generated by nozzles 44 illustrated in FIG. 1 as falling downwardly by the action of gravity inside open tower 2, are collected directly in the funnel portion 96, prior to mixing with the absorption liquid contained in the absorption liquid tank 8. The collected liquid droplets then flow via fluidly connected pipe 64, to the first pH sensor 66 and the first sulphite sensor 68 for analysis.

The solubility of sulphite is higher at lower pH-values. The absorption liquid captured by the scoop 60 normally has a lower pH value than the absorption liquid in the tank 8, because the absorption liquid captured by the scoop 60 has just contacted sulphur dioxide, causing an acidification. Typically, the absorption liquid in the tank 8 would have a pH of 5.5 to 6.0, while the absorption liquid captured by the scoop 60 would have a pH of 3-5. A high concentration of sulphite in the tank 8 may be concealed by a portion of the sulphite precipitated on limestone particles at the relatively high pH prevailing in the tank 8. Hence, it is easier to detect high concentrations of sulphite with a high level of accuracy in the absorption liquid captured by the scoop 60, than in the absorption liquid in the tank 8.

Figure 2B:
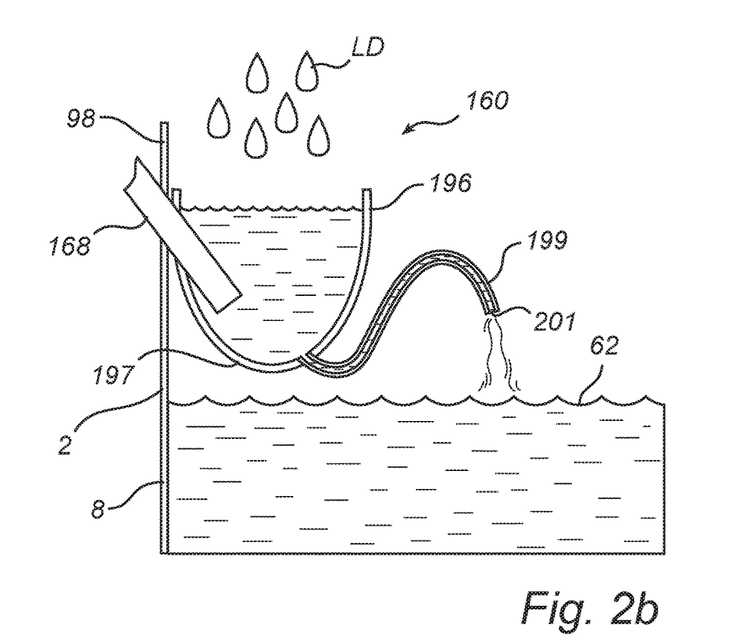
FIG. 2b is an enlarged schematic side cross sectional view of a scoop according to an alternative embodiment.

FIG. 2b illustrates a scoop 160 according to an alternative embodiment. The scoop 160 is positioned entirely within the open tower 2 and comprises a funnel portion 196 arranged inside the open tower 2, above the surface 62 of absorption liquid contained in the absorption liquid tank 8. Liquid droplets LD generated by nozzles 44 illustrated in FIG. 1 as falling downwardly inside open tower 2 are collected in the funnel portion 196. The funnel portion 196 is connected, at a bottom 197 thereof, to an "S"-shaped drain pipe 199. The drain pipe 199 functions as a water trap ensuring that an amount of collected liquid is present in funnel portion 196. A mouth 201 of the drain pipe 199 opens above the surface 62 to avoid any siphoning effects. A first sulphite sensor 168 extends into the open tower 2 and into the collected absorption liquid in the funnel portion 196. The funnel portion 196 and the drain pipe 199 ensure that first sulphite sensor 168 measures the sulphite concentration in freshly collected absorption liquid.

Figure 3:
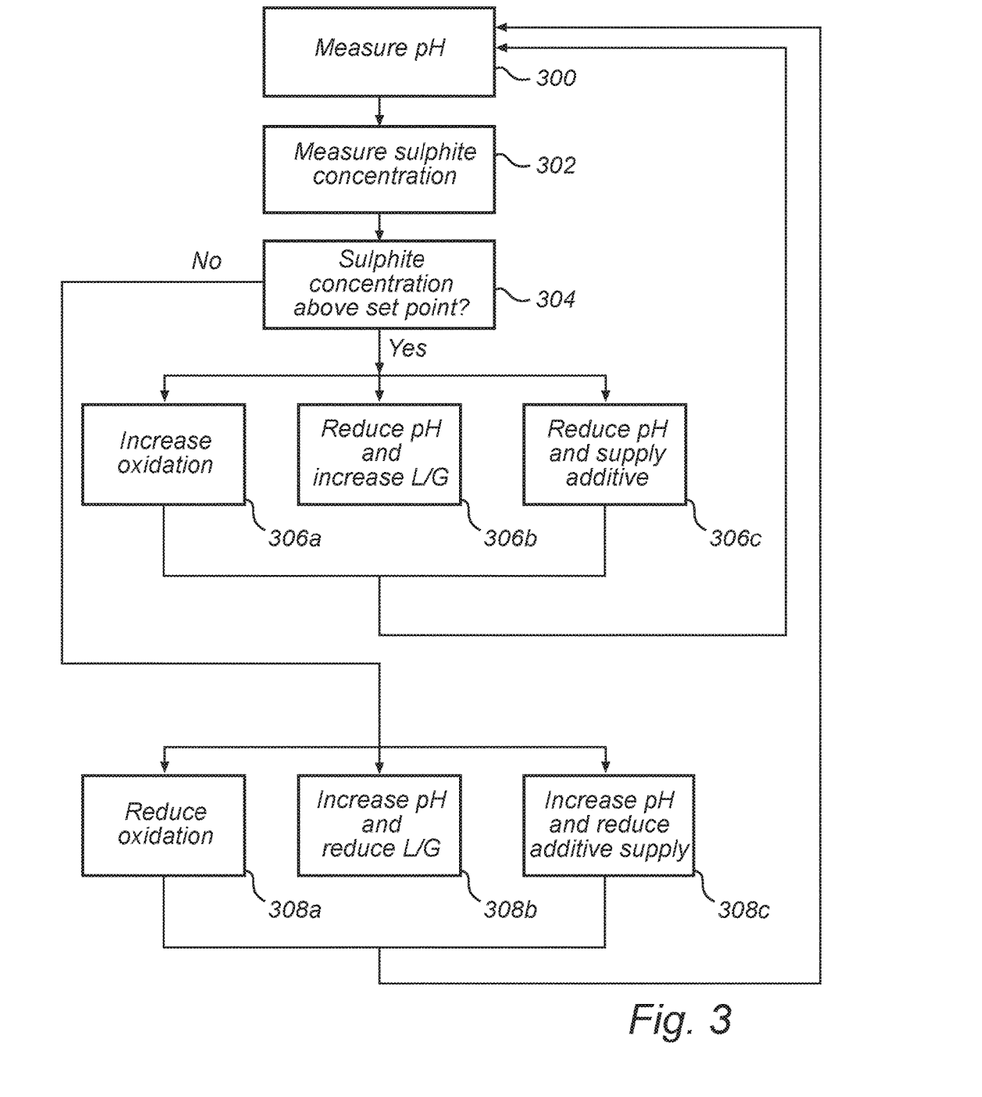
FIG. 3 is a flow chart illustrating a first method of controlling the operation of a wet scrubber.

FIG. 3 illustrates in the form of a flow chart a first method embodiment of controlling the operation of the wet scrubber 1 illustrated in FIG. 1.

In a step 300 of the method, the pH of the limestone absorption liquid is measured. This could be performed by means of the first pH sensor 66 and/or the second pH sensor 72. Signals indicating the measured pH value could be sent, as depicted in FIG. 1, from the first pH sensor 66 and/or the second pH sensor 72 to the control unit 52.

In a step 302 the concentration of sulphite of the limestone absorption liquid is measured. This could be performed by means of the first sulphite sensor 68 and/or the second sulphite sensor 74. Signals indicating the measured concentration of sulphite could be sent, as depicted in FIG. 1, from first sulphite sensor 68 and/or second sulphite sensor 74 to the control unit 52. First sulphite sensor 68 would give direct information of the absorption process that has occurred in the tower 2 in a feed-back manner, while the second sulphite sensor 74 would give information regarding the absorption liquid forwarded to the nozzles 44 in a feed-forward manner. Depending on the operating conditions, and in particular the variations in the operating conditions, the data from first sulphite sensor 68 may be more or less relevant compared to the data from second sulphite sensor 74. The combined data from first and second sulphite sensors 68 and 74 provide the most complete information about the process occurring in tower 2.

In a step 304 the control unit 52, depicted in FIG. 1, analyses the measured concentration of sulphite.

Without being bound by any theory, it is believed that a high sulphite concentration in the limestone absorption liquid may cause a blinding of the limestone, $CaCO_3$. As used herein, the term "blinding" means that calcium sulphite, $CaSO_3$, is precipitated in solid form on limestone particles, making the limestone particles more difficult to dissolve in water, according to [eq. 1]. Hence, blinding of the limestone particles is believed to cause a reduced utilization of the limestone supplied from the absorbent supply system 22, and, hence, increased operating costs, and a reduced quality of the gypsum produced. A set point for the sulphite concentration in the limestone absorption liquid is established, based on empirical tests, and/or calculations, to a concentration at which blinding of the limestone is at acceptably low levels. The set point for the sulphite concentration may be plant specific, and may depend on such factors as temperature of the process gas, intended operating pH of the absorption liquid, type of limestone, requirements with regard to acceptable levels of impurities in the gypsum produced, etc. Typically, the set point for the sulphite concentration is somewhere in the range of 0.1 to 5 g sulphite (as $SO_3^{2-}$) per liter of absorption liquid.

Continuing with the description of step 304, the measured concentration of sulphite is compared to the set point for the sulphite concentration, to determine whether or not the measured concentration of sulphite is higher than the set point. If the result of such comparison is "YES", i.e., that the measured sulphite concentration is higher than the set point for the sulphite concentration, then measures are taken to reduce the concentration of sulphite in the limestone absorption liquid. FIG. 3 depicts three different steps 306a, 306b and 306c that may be used, alone or in combination, to reduce the concentration of sulphite in the limestone absorption liquid.

Step 306a involves increasing the level of oxidation by increasing the supply of oxygen containing gas, such as air, to the absorption liquid tank 8 by the oxidation arrangement 10. For example, the blower 12 could be operated at a higher rpm, or, as an alternative, a further blower could be started to increase the supply of oxygen containing gas to the absorption liquid tank 8. The effect of such an increase in the oxidation is a reduction in the concentration of sulphite in the limestone absorption liquid, at the cost of an increased amount of energy consumed by the blower 12.

Step 306b involves reducing the pH of the limestone absorption liquid. Such may be achieved by the control unit 52 sending a signal to the control valve 90 depicted in FIG. 1 within limestone supply pipe 32 to effect a reduction of the amount of limestone slurry supplied to the absorption liquid tank 8 from the mixing tank 28 via the fluidly connected supply pipe 32. A reduction in the pH of the limestone absorption liquid, for example a reduction from pH 5.8 to pH 5.5, causes an increase in the rate of oxidation, hence reducing the concentration of sulphite in the limestone absorption liquid. A reduction in the pH of the limestone absorption liquid may result in reduced removal efficiency with regard to the absorption of sulphur dioxide, $SO_2$, from the flue gas F inside open tower 2. To compensate for such reduced removal efficiency, step 306b further involves an increase in the liquid to gas ratio, L/G, inside the wet scrubber tower 2. Such may be achieved by the control unit 52 sending a signal to the scrubber circulation pump 34 to cause an increased flow of limestone absorption liquid being pumped to the nozzles 44 to be atomized thereby and subsequently brought into contact with the flue gas F. Such increased flow of limestone absorption liquid compensates for the reduced pH, at the cost of an increased amount of energy consumed by the pump 34. As alternative to increasing the flow of the pump 34, a further scrubber circulation pump could be started.

Step 306c involves reducing the pH of the limestone absorption liquid, in a similar manner as in step 306b. To compensate for reduced removal efficiency at such lower pH, step 306c further involves supplying an absorption enhancing additive, such as adipic acid, to the limestone absorption liquid. Such may be achieved by the control unit 52 sending a signal to an additive supply system in the form of an adipic acid tank 102 depicted in FIG. 1 and supplying adipic acid to the absorption liquid tank 8 via a fluidly connected supply pipe 104. Such supply of absorption enhancing additive to the limestone absorption liquid compensates for the reduced pH, at the cost of increased operating costs.

Optionally, other absorption enhancing additives could be supplied to the absorption liquid from the tank 102. The absorption enhancing additives could be of various types, and enhance the absorption in various ways. Examples of absorption enhancing additives include:

oxidation enhancing additives, such as Fe, Mn, Co, Cu, and sulphite oxidizing enzymes, buffering additives, such as adipic acid, formic acid, acetic acid, sulfopropionic acid, sulfosuccinic acid, and alkali additives, such as $Na_2CO_3$, MgO, $MgSO_4$.

Oxidation enhancing additives enhance the oxidation of sulphite in the absorption liquid. Buffering additives buffer the absorption liquid, meaning that pH of an absorption liquid droplet drops less as the droplet moves downwardly through the tower 2. Alkali additives increase the alkalinity of the absorption liquid, thereby increasing the removal efficiency.

An example of sulphite oxidizing enzymes is the sulphite oxidase type of enzymes. A sulphite oxidase may be prepared in accordance with the article "*Optimization of expression of human sulfite oxidase and its molybdenum domain*" by C A Temple, T N Graf, and K V Rajagopalan, published in Arch Biochem Biophys. 2000 Nov. 15; 383(2):281-7.

After one or more of steps 306a-c have been conducted, the method returns to step 300 to check if conducted measures have been sufficient, or if a further reduction of the sulphite concentration is required, by any of steps 306a-c.

If the result of the comparison in step 304 is "NO", i.e., that the measured sulphite concentration is not higher than the set point for the sulphite concentration, then measures are taken to increase the concentration of sulphite in the limestone absorption liquid. FIG. 3 depicts three different steps 308a, 308b and 308c that may be used, alone or in combination, to increase the concentration of sulphite in the limestone absorption liquid. Increasing the concentration of sulphite is normally no benefit per se, but it is linked to reduced operating costs.

Step 308a involves reducing the oxidation by reducing the supply of oxygen containing gas, such as air, to the absorption liquid tank 8 by the oxidation arrangement 10. For example, the blower 12 could be operated at a lower rpm, or, as an alternative, if several parallel blowers are used, one or more of those blowers could be stopped. The effect of such reduction in the oxidation is a reduced amount of energy consumed by the blower 12.

Step 308b involves increasing the pH of the limestone absorption liquid. Such may be achieved by the control unit 52 sending a signal to a control valve 90 depicted in FIG. 1 within limestone supply pipe 32 to cause an increase of the amount of limestone slurry supplied to the absorption liquid tank 8 from the mixing tank 28 via the fluidly connected supply pipe 32. An increase in the pH of the limestone absorption liquid, for example an increase from pH 5.8 to pH 6.0, causes an increase in the removal efficiency with regard to the absorption of sulphur dioxide, $SO_2$, from the flue gas F inside the open tower 2. Such increased removal efficiency makes it possible to reduce the liquid to gas ratio, L/G, inside the wet scrubber tower 2. Such may be achieved by the control unit 52 sending a signal to the scrubber circulation pump 34 to cause a reduced flow of limestone absorption liquid being pumped to the nozzles 44 to be atomized thereby and subsequently brought into contact with the flue gas F. Such reduced flow of limestone absorption liquid reduces the amount of energy consumed by the pump 34. As alternative to reducing the flow of the pump 34, a further scrubber circulation pump could be stopped.

Step 308c involves increasing the pH of the limestone absorption liquid, in a similar manner as in step 308b. Such increase may be coupled to reducing, or even stopping, the supply of an absorption enhancing additive, such as adipic acid, to the limestone absorption liquid. Such may be achieved by the control unit 52 sending a signal to an adipic acid tank 102 depicted in FIG. 1 and supplying adipic acid to the absorption liquid tank 8 via a fluidly connected supply pipe 104. Reducing or stopping the supply of adipic acid reduces operating costs.

After one or more of steps 308a-c have been conducted, the method returns to step 300 to check if conducted measures have been sufficient, if a further increase of the sulphite concentration is possible, by any of steps 308a-c, or if a reduction of the sulphite concentration is required, by any of steps 306a-c.

The method described with reference to FIG. 3 utilizes the measurement of the concentration of sulphite to operate the wet scrubber as economically as at all possible, without risking limestone blinding.

Figure 4:
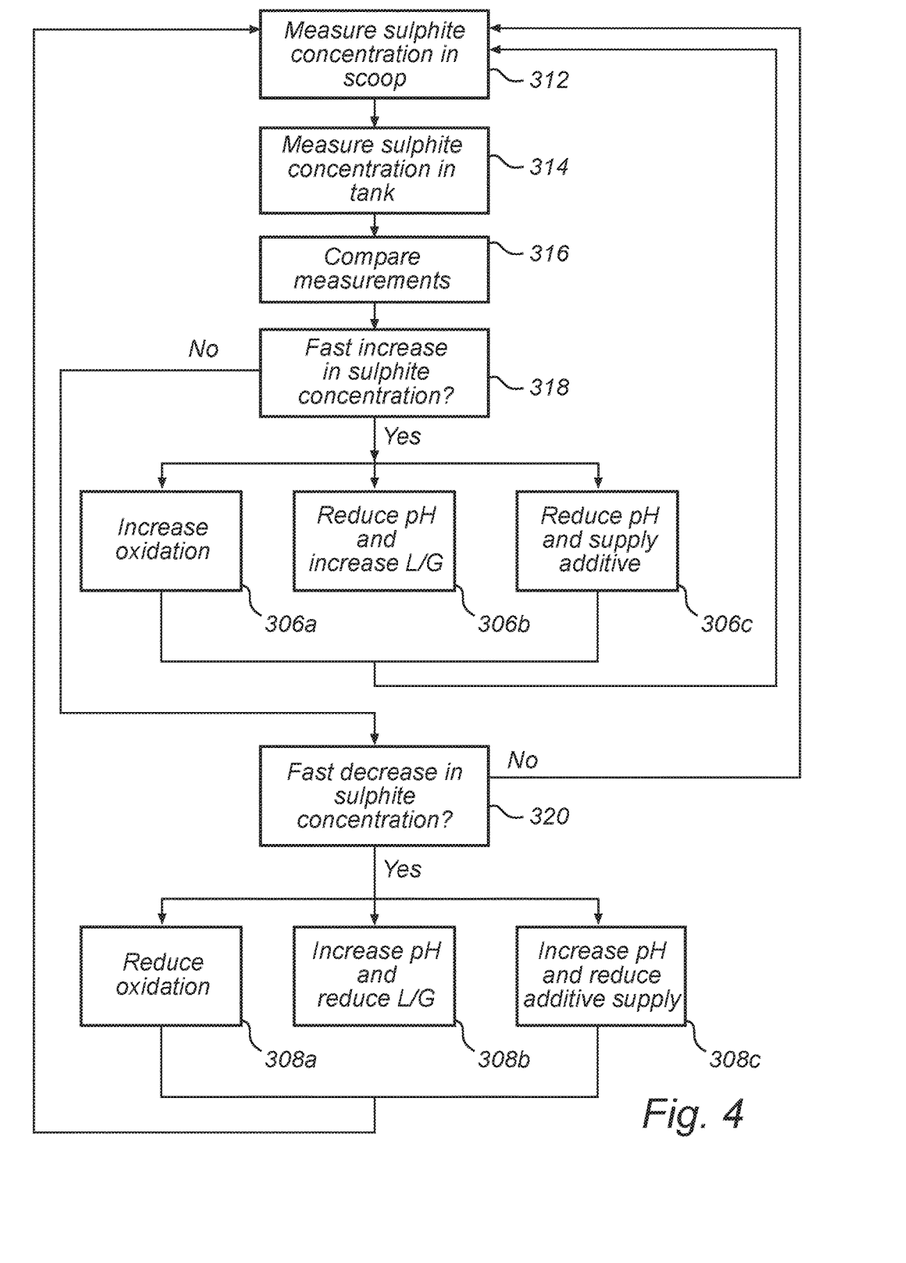
FIG. 4 is a flow chart illustrating a second method of controlling the operation of a wet scrubber.

FIG. 4 illustrates a second method embodiment of controlling the operation of the wet scrubber 1 illustrated in FIG. 1. This second method may be used alone, or in combination with the method illustrated in FIG. 3 to increase the responsiveness to fast process variations.

In a step 312 a first concentration of sulphite of the limestone absorption liquid falling downwardly inside tower 2 is measured. This could be performed by means of the first sulphite sensor 68 measuring the concentration of sulphite in the absorption liquid captured in the scoop 60 illustrated in FIG. 2a. Signals indicating the measured first concentration of sulphite could be sent, as depicted in FIG. 1, from first sulphite sensor 68 to the control unit 52.

In a step 314 a second concentration of sulphite of the limestone absorption liquid in the tank 8 is measured. This could be performed by means of the second sulphite sensor 74. Signals indicating the measured second concentration of sulphite could be sent, as depicted in FIG. 1, from the second sulphite sensor 74 to the control unit 52.

In step 316 the measured first concentration of sulphite in the absorption liquid as measured in the scoop 60 by means of sensor 68 is compared to measured second concentration of sulphite in the absorption liquid as measured in the tank 8. Such comparison could be performed by the control unit 52.

The absorption liquid captured by the scoop 60 just passed through the open tower 2 and is a good indicator of the absorption process occurring at the moment inside the open tower 2. The sulphite concentration measured by the first sulphite sensor 68 is indicative of the future oxidation level requirements in the tank 8. The sulphite concentration measured by the second sulphite sensor 74 is indicative of the present function of the oxidation in the tank 8. For example, if the sulphite concentration measured by the first sulphite sensor 68 increases rapidly, while the sulphite concentration measured by the second sulphite sensor 74 remains at its original low level, such is an early indication of a rapid increase in the amount of sulphur dioxide in the flue gas F entering the open tower 2 via the inlet 4, and, hence, an early indication of a future need for increased oxidation in the tank 8. Similarly, if the sulphite concentration measured by the first sulphite sensor 68 falls rapidly, while the sulphite concentration measured by the second sulphite sensor 74 remains at its original level, such is an early indication of a rapid decrease in the amount of sulphur dioxide in the flue gas F entering the open tower 2 via the inlet 4, and, hence, an early indication of a reduced oxidation capacity.

Furthermore, rapid changes in the level of oxidation by the oxidation arrangement 10, or in the natural oxidation, i.e., the oxidation that occurs independently of the oxygen containing gas supplied from blower 12, may also be detected as a change in the concentration of sulphite. For example, some metals, such as manganese, Mn, and iron, Fe, are known for enhancing the natural oxidation effect. If such metals would be precipitated, due to altered chemical conditions in the absorption liquid, a reduced natural oxidation would result, which would require measures to increase the oxidation. For example, if the sulphite concentration measured by the first sulphite sensor 68 is stable, while the sulphite concentration measured by the second sulphite sensor 74 increases, such is an early indicator of problems with the oxidation, which may be due to, for example, a reduced natural oxidation or problems with the blower 12 of the oxidation arrangement. Such an early indication could trigger a check of the function of the blower 12, or trigger an increase in the level of oxidation of the blower 12, if the natural oxidation appears to be the problem. Similarly, if the sulphite concentration measured by the first sulphite sensor 68 is stable, while the sulphite concentration measured by the second sulphite sensor 74 decreases rapidly, such is an early indicator of an enhanced natural oxidation. Such an early indication could trigger a reduction in the level of oxidation of the blower 12, to save energy. When determining whether an increased or reduced concentration of sulphite is due to an increased or reduced concentration of sulphur dioxide in the flue gas F, or due to a changed oxidation process, the control unit 52 may also compare signals from first $SO_2$ sensor 92 and/or second $SO_2$ sensor 94 to determine whether the concentration of sulphur dioxide in the flue gas F has changed.

In step 318 it is determined whether or not the comparison in step 316 indicates a quick increase in the concentration of sulphite in the limestone absorption liquid. If the answer to the question of step 318 is "YES", i.e., that the concentration of sulphite increases rapidly, then one or more of the steps 306a-c described in detail above with reference to FIG. 3, may be implemented to reduce the concentration of sulphite in the limestone absorption liquid.

If the answer to the question of step 318 is "NO", then step 320 is implemented. In step 320 it is determined whether or not the comparison in step 316 indicates a quick reduction in the concentration of sulphite in the limestone absorption liquid. If the answer to the comparison of step 320 is "YES", i.e., that the concentration of sulphite decreases quickly, then one or more of the steps 308a-c described in detail above with reference to FIG. 3, may be implemented to reduce the operating cost of the wet scrubber 1.

According to one embodiment the method described with reference to FIG. 4 may be implemented independently in the control unit 52. According to another embodiment the method of FIG. 3 may be implemented as a base method of controlling the operation of the wet scrubber 1, with the method of FIG. 4 being implemented as a complement to provide a faster response in the control of the wet scrubber 1 in situations of rapid increases or reductions in the concentration of sulphite in the limestone absorption liquid. Hence, for example, if a rapid increase in the concentration of sulphite is detected, then the measures, i.e., one or more of steps 306a-c, to reduce the concentration of sulphite may be initiated even if the concentration of sulphite is not yet above the set point as dictated by the method of FIG. 3. Similarly, if a rapid decrease in the concentration of sulphite is detected, then the measures, i.e., one or more of steps 308a-c, to reduce the operating costs may be initiated even if the concentration of sulphite is not yet below the set point.

Figure 5:
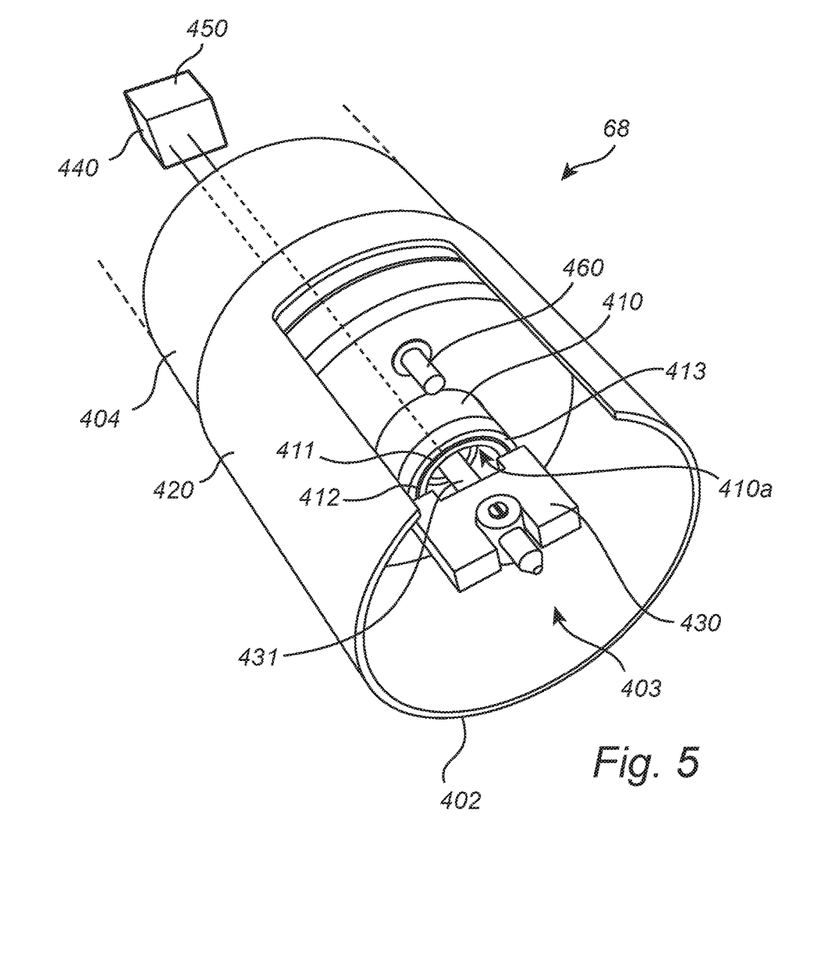
FIG. 5 is a perspective view of a sulphite sensor.
Figure 6:
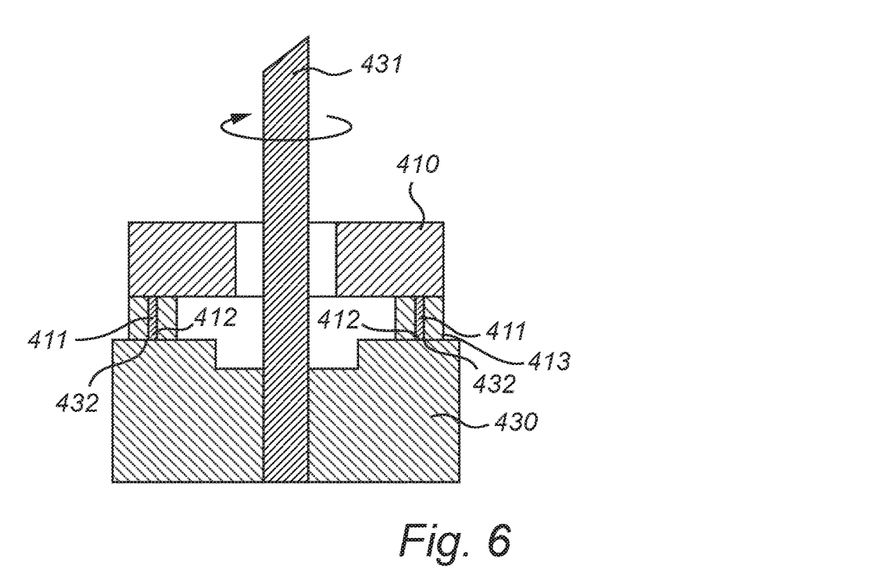
FIG. 6 is a schematic cross-sectional side view of a sulphite sensor.

FIG. 5 illustrates in a perspective view an example of a design of the sulphite sensor 68, and FIG. 6 illustrates the sulphite sensor 68 in a schematic cross-sectional side view. Sulphite sensors 74 and 168 may be of a similar or different design. The sulphite sensor 68 comprises a base section 404, and a cover 402 that forms sides of a space 403 for sulphite detection. A sensor head 410 is located in the space 403. The sensor head 410 is formed as a tube extending into the space 403. At an axial end portion 413 of the sensor head 410, a first electrode 411 having the form of a platinum ring is provided. A surface 412 of the first electrode 411 is level with the axial end portion 413 of the sensor head 410.

A shaft 431 extends through interior 410a of the tube shaped sensor head 410. The shaft 431 is rotated by an electric motor (not shown). The shaft 431 is coupled to a grinding unit 430. The grinding unit 430 has a surface 432, which is best shown in FIG. 6, adapted to abut the surface 412 of the first electrode 411. The shaft 431 rotates the grinding unit 430 such that the surface 432 of the grinding unit 430 grinds/cleans the surface 412 of the first electrode 411. The grinding unit 430 rotates in contact with the surface 412 of the first electrode 411 at a speed of 2-40 rpm, preferably at a speed of 15 rpm. The grinding unit 430 is preferably made of a ceramic material based on e.g. silicon carbide or silicon nitride.

The sulphite sensor 68 further comprises a second electrode 420. The second electrode 420 is preferably of a metal, such as steel or the like. The second electrode 420 is located at a distance from the first electrode 411. In the illustrated embodiment, the second electrode 420 is constituted by the metal cover 402.

A control unit 440 is arranged in the sulphite sensor 68 or connected to the sulphite sensor 68 and is adapted to send voltage pulses through the substance occupying the space between the first electrode 411 and the second electrode 420. When the sulphite sensor 68 is submerged into a substance, the voltage pulses enter the substance via the first electrode 411. The second electrode 420 is adapted to receive current responses generated by said voltage pulses and pass the current responses back to the control unit 440. The control unit 440 receives and analyzes using an analyzing unit 450 the current responses and calculates a concentration of sulphite in the substance using a multivariate data analysis. By using multivariate data analysis in the analyzing unit 450, mathematical models from samples with known sulphite concentrations is used for creating a prediction model that is used for determining the sulphite concentration in an unknown substance.

Data from voltammetric measurements are often difficult to interpret. Each measurement consists of a number of variables. Multivariate data analyzing methods, such as principal component analysis (PCA) and projection to latent structure (PLS), as is known from, for example: Wold, S., Esbensen, K. and Geladi, P. "Principal component analysis: A tutorial." Chemometrics and Intelligent Laboratory Systems 2, 37-52, 1987; and from: S. Wold, M. Sjöström and L. Eriksson "PLS-regression: a basic tool of chemometrics" Chemometrics and Intelligent Laboratory Systems, 58 (2001) 109-130, have shown to be useful. PCA is a mathematical tool, which describes the variance in experimental data. A vector is calculated which describes the direction of the largest variance in experimental data, that is the direction that describes the largest differences between observations. This vector is called the first principal component. The second principal component is orthogonal to and thus independent of the first principal component. Further principal components can be calculated in a similar way, until most of the observations are explained. A new matrix, as defined by the principal components is then formed, and the data set is considerably reduced, depending on the significance of the different principal components, but in many cases only to two dimensions. The loading vectors describe the direction of the principal components in relation to the original variables, and the score vectors, describe the direction of the principal components in relation to the observations. Thus, a score plot can be made, showing the relationships between the original samples and how much they influence the system. Thus, a score plot shows the relationships between the experiments, and groupings of them can be used for classification.

PLS is used to make models from calibration sets of data. It is a linear method, in which PCA is performed on both the X-data (the voltammogram) and the Y-data (the concentrations). Then a linear regression is performed on each PC between the datasets and the Y-data, giving a regression model. This model can be used to predict values from the voltammograms.

Further information regarding multivariate data analysis may be found in I. T. Jolliffe "Principle Component Analysis" Springer-Verlag, New York inc. (1986) ISBN 0-387-96269-7, or K. R. Beebe, R. J. Pell and M. B. Seasholtz "Chemometrics—A practical guide" John Wiley & Sons Inc. (1998) ISBN 0-471-12451-6.

In one embodiment, the sulphite sensor 68 further comprises a temperature sensor 460 for measuring the temperature of the substance.

Figure 7:
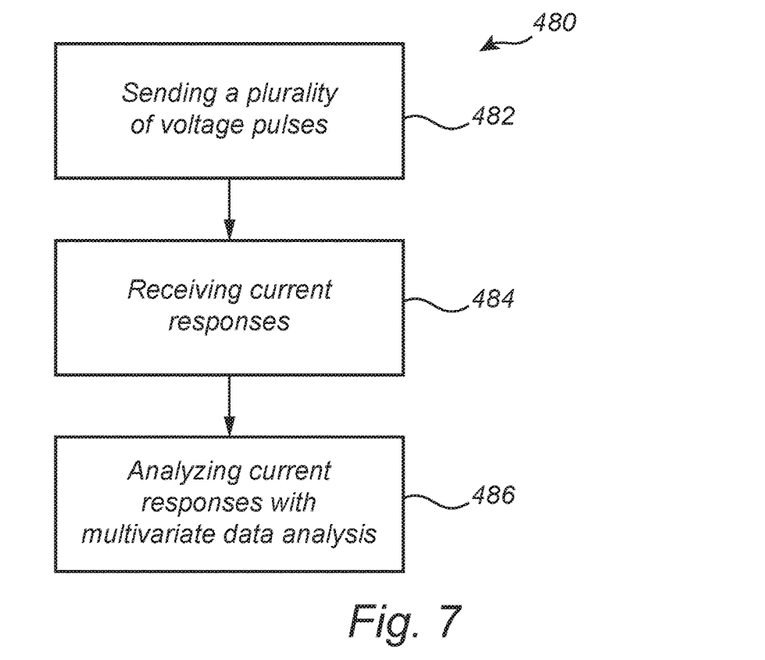
FIG. 7 is a flow chart of a method of measuring sulphite.
Figure 8A:
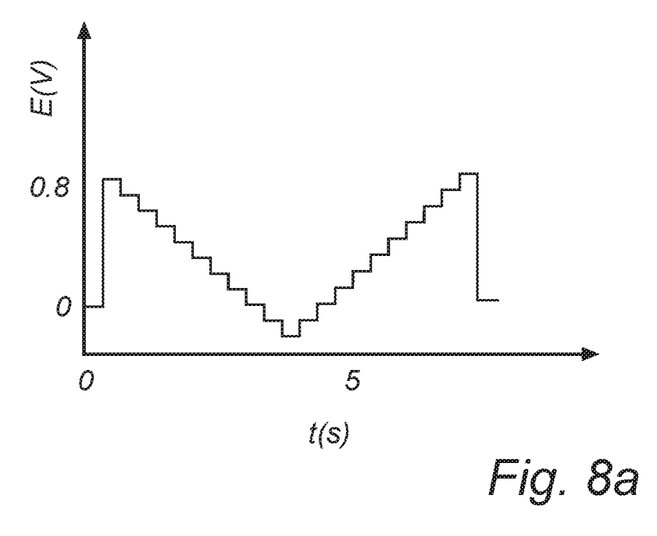
FIG. 8a is a graph of voltage level over time from a method of measuring sulphite.

FIG. 7 is a flow chart of a method 480 for measuring a concentration of sulphite in a substance. The substance may be provided in a gas cleaning process. In a step 482, a plurality of voltage pulses is sent through the first electrode 411. The first electrode 411 is in contact with the substance. Voltage pulses are sent from the control unit 440 by the first electrode 411 and the second electrode 420 through the substance as a stepwise increasing or decreasing voltage level as shown in FIG. 8a. A staircase pattern of the voltage level sent through the first electrode 411 is formed. Each step involves increasing or decreasing the voltage level by, preferably, about 0.05 V. In an example of the method, the voltage level sent through the substance as voltage pulses is, in a stepwise manner, increased from a voltage level of −1.0 V to a voltage level of 1.0 V in steps of 0.05 V. In a further example, illustrated in FIG. 8a, the voltage level is first decreased from 0.8 V and down to −0.1 V, in steps of 0.05 V, and is then increased from −0.1 V and up to 0.8 V, in steps of 0.05 V.

In a step 484, current responses are received, which current responses are generated by the voltage pulses sent by the first electrode 411 to the second electrode 420. The current responses are received by the second electrode 420. The second electrode 420 is also in contact with the substance. Each step of increasing or decreasing the voltage level generates a new current response in the second electrode 420.

In a final step 486, the current responses are analyzed using a multivariate data analysis. The concentration of sulphite in the substance may thereby be measured based on the current responses. According to one embodiment, all of the plurality of current responses is used for the measurement of sulphite concentration in the substance. In one embodiment, the current response is analyzed after each sent voltage pulse. Alternatively, a series of voltage pulses are sent, generating a series of current responses, before multivariate data analysis is performed on the series of current responses.

Figure 8B:
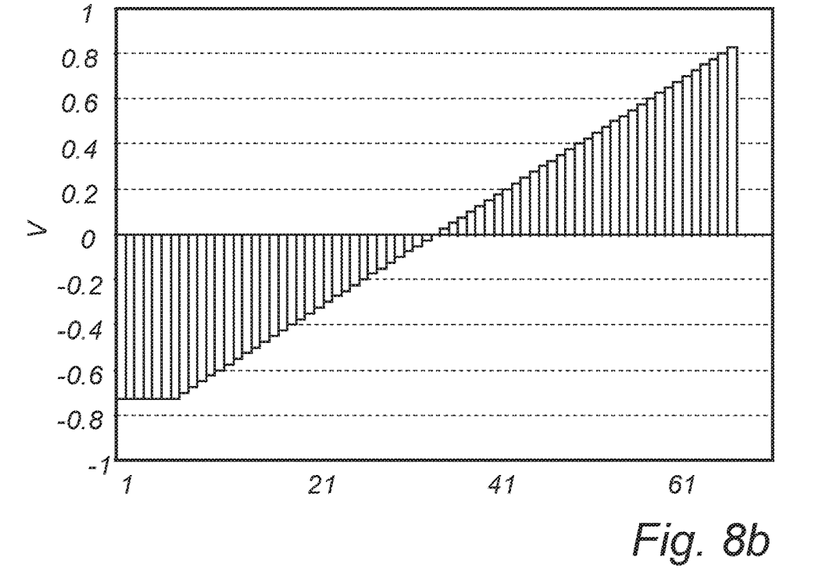
FIG. 8b is a simulation plot of voltage level pulses from a method of measuring sulphite.
Figure 8C:
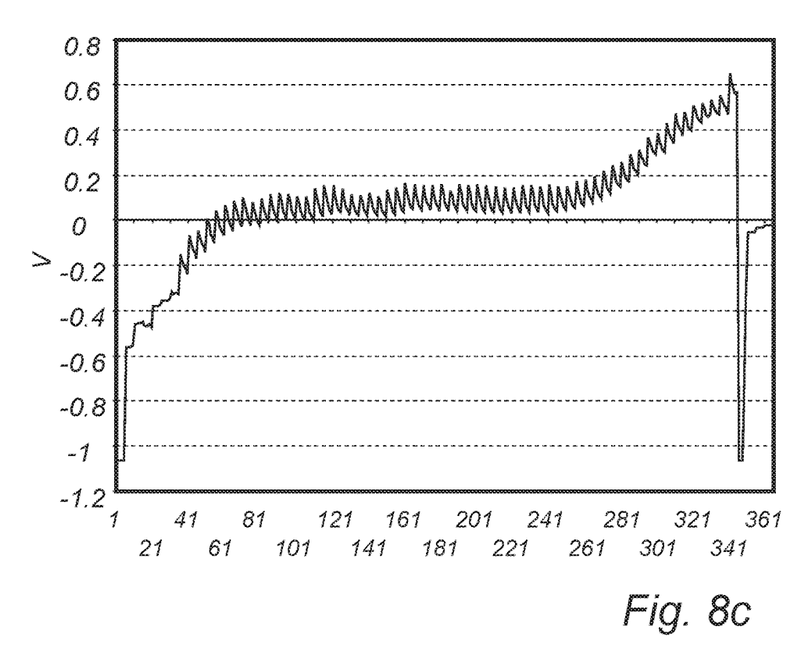
FIG. 8c is a simulation plot of a voltage corresponding to a current response generated by voltage pulses in FIG. 8b.

FIG. 8b further shows an example simulation of voltage pulses in a staircase pattern. The voltage level varies over time from approximately −0.75 V to approximately 0.8 V. The values on the x axis represent number of voltage pulses. FIG. 8c shows corresponding current responses as an outgoing voltage from an electronic circuit. Information from the current responses is used for estimating the sulphite level in the substance, using multivariate data analysis. Each voltage pulse as shown in FIG. 8b corresponds to five measured voltage values in FIG. 8c. Hence, in the example shown in FIGS. 8b and 8c, the response of each voltage pulse is measured five times during each voltage pulse. The values on the x axis of FIG. 8c represent number of measurements.

It will be appreciated that numerous variants of the embodiments described above are possible within the scope of the appended claims.

Hereinbefore it has been described that the control unit 52 and the method of controlling the operation of a wet scrubber is applied to a wet scrubber 1 of the tower type. It will be appreciated that the control unit 52 and the method of controlling the operation of a wet scrubber may also be applied to other types of wet scrubbers utilized for removing sulphur dioxide from a process gas. One such alternative type of wet scrubber is a bubbling bed scrubber, an example of which is disclosed in WO 2005/007274. The bubbling bed scrubber comprises an absorption vessel comprising a perforated plate carrying on its upper side a layer of absorption liquid through which absorption layer the process gas is bubbled. If a reduction in pH is initiated to reduce blinding of limestone, then such pH reduction may, in the bubbling bed scrubber, be accompanied by an increase in the height of the bubbling bed, to maintain desired removal efficiency with regard to the absorption of sulphur dioxide, $SO_2$, also at such lower pH. An increased height of the bubbling bed is achievable by controlling an absorption liquid supply device, such as a pump supplying absorption liquid to the bubbling bed, or a throttle throttling a drain from the bubbling bed, resulting in an increased liquid to gas ratio, similar to what may, as described hereinbefore, be achieved by controlling the pump 34 of the wet scrubber tower 2.

Hereinbefore it has been described that the absorption liquid tank 8 is arranged at the bottom of the vertical open tower 2, and that oxygen containing gas and limestone are supplied thereto. It will be appreciated that the absorption liquid tank 8 could, as alternative, be located beside the open tower 2. Furthermore, it is also possible to divide the absorption liquid tank 8 into one tank arranged for oxidation, and one tank for supply of limestone, with one or both of these tanks being located outside of the open tower 2.

Hereinbefore it has been described that limestone, $CaCO_3$, is used as absorbent material. It will be appreciated that other absorbent materials could also be utilized. Examples of such other materials include dolomite, $CaMg(CO_3)_2$, and other absorbent materials that are suitable for removal of sulphur dioxide.

Hereinbefore it has been described that a measured concentration of sulphite exceeding the set point therefore may be compensated for by reducing the pH or increasing the level of oxidation of an oxidation arrangement. In accordance with an alternative embodiment, an absorption enhancing additive, such as adipic acid, manganese, Mn, iron, Fe, and/or oxidizing enzyme, may be supplied to the absorption liquid to reduce the concentration of sulphite and/or enhance the absorption capacity. The measure of supplying the absorption enhancing additive could be used alone, or in combination with one or more other measures, such as that of increasing the duty of an oxidation arrangement.

Hereinbefore it has been described that a gas containing oxygen is supplied to the absorption liquid by means of a blower 12. It will be appreciated that other per se known devices may also be utilized for this purpose. Examples of such other devices include agitators drawing air or other suitable oxygen containing gas into the absorption liquid, ejectors drawing oxygen containing gas into the absorption liquid, combinations of blower and agitator, etc.

To summarize, a wet scrubber 1 for cleaning a process gas containing sulphur dioxide comprises an absorption vessel 2 operative for contacting the process gas with absorption liquid to absorb sulphur dioxide from the process gas, a sensor 68, 74 for measuring a concentration in the absorption liquid, and a control unit 52. The control unit 52 receives a measurement signal from the sensor 68, 74 to control, based on the measured concentration, at least one wet scrubber operating parameter influencing the concentration in the absorption liquid.

While the invention has been described with reference to a number of preferred embodiments, it will be understood by those skilled in the art that various changes may be made and equivalents may be substituted for elements thereof without departing from the scope of the present invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A method of controlling a wet scrubber used to clean a process gas containing sulphur dioxide, the method comprising:
    contacting the process gas with an absorption liquid in an absorption vessel to absorb sulphur dioxide from the process gas;
    measuring a concentration of sulphite in the absorption liquid to obtain a sulphite concentration measurement; and
    controlling, based on the sulphite concentration measurement as compared to a set point therefor, at least one scrubber operating parameter influencing the concentration of sulphite in the absorption liquid, by effecting, when the sulphite concentration measurement exceeds the set point, a reduction of a pH of the absorption liquid accompanied by at least one of:
        increasing a liquid to gas ratio in the absorption vessel; and
        increasing a supply of an absorption enhancing additive to the absorption liquid.

2. The method according to claim 1, further comprising:
    effecting, when the sulphite concentration measurement exceeds the set point, at least one of:
        increasing a supply of a gas containing oxygen to the absorption liquid;
        supplying an absorption enhancing additive to the absorption liquid.

3. The method according to claim 1, further comprising:
    effecting, when the sulphite concentration measurement is below the set point, at least one of:
        reducing a supply of a gas containing oxygen to the absorption liquid;
        increasing a pH of the absorption liquid; and
        reducing a supply of an absorption enhancing additive to the absorption liquid.

4. The method according to claim 1, further comprising:
    effecting, when the sulphite concentration measurement is below the set point, an increase of a pH of the absorption liquid accompanied by at least one of:

reducing a liquid to gas ratio in the absorption vessel; and reducing a supply of an absorption enhancing additive to the absorption liquid.

5. The method according to claim 1, further comprising:

collecting absorption liquid after sulphur dioxide absorption by the absorption liquid from the process gas; and measuring a sulphite concentration of the collected absorption liquid to obtain a sulphite concentration measurement prior to mixing the absorption liquid with absorbent material.

6. The method according to claim 1, further comprising:

collecting absorption liquid after sulphur dioxide absorption by the absorption liquid from the process gas; and measuring a sulphite concentration of the collected absorption liquid to obtain a sulphite concentration measurement prior to mixing the absorption liquid with absorbent material and prior to bubbling an oxygen containing gas through the absorption liquid.

7. The method according to claim 1, further comprising:

collecting absorption liquid after sulphur dioxide absorption by the absorption liquid from the process gas; and measuring the concentration of sulphite within 1 minute of collecting the absorption liquid from the absorption vessel.

8. The method according to claim 1, further comprising:

collecting absorption liquid after sulphur dioxide absorption by the absorption liquid from the process gas and prior to bubbling an oxygen containing gas through the absorption liquid;

measuring a first concentration of sulphite of the collected absorption liquid to obtain a first measurement;

collecting absorption liquid after the absorption liquid is exposed to a bubbling of oxygen containing gas;

measuring a second concentration of sulphite of the exposed absorption liquid to obtain a second measurement, and comparing the first measurement to the second measurement to determine whether the concentration of sulphite is increasing or decreasing.

9. The method according to claim 1, further comprising:

detecting, based on a comparison between a first sulphite concentration measurement and a second sulphite concentration measurement, if the sulphite concentration of the absorption liquid is increasing; and effecting, when the sulphite concentration is increasing, at least one of:
  increasing a supply of a gas containing oxygen to the absorption liquid;
  reducing a pH of the absorption liquid; and
  supplying an absorption enhancing additive to the absorption liquid.

* * * * *